(12) United States Patent
Schleipman et al.

(10) Patent No.: US 6,391,057 B1
(45) Date of Patent: May 21, 2002

(54) DILATING OCULAR PROSTHESIS

(76) Inventors: Fredrick Schleipman, 66 Partridge Hill, Norwich, VT (US) 05055; Russell Schleipman, 37 Union Park, Boston, MA (US) 02118; David P. Van Sleet, Rte. 5, Norwich, VT (US) 05055; Paul A. Duncanson, 171 Webster Ave., Franklin, NH (US) 03235

( * ) Notice: Subject to any disclaimer, the term of this patent is extended or adjusted under 35 U.S.C. 154(b) by 42 days.

(21) Appl. No.: 09/698,775

(22) Filed: Oct. 27, 2000

Related U.S. Application Data

(63) Continuation-in-part of application No. 09/262,217, filed on Mar. 4, 1999, now Pat. No. 6,139,577.

(51) Int. Cl.[7] .............................................. A61F 2/14
(52) U.S. Cl. ................................... 623/6.64; 446/389
(58) Field of Search ............................... 623/6.64, 4.1; 446/389, 175

(56) References Cited

U.S. PATENT DOCUMENTS

| | | | |
|---|---|---|---|
| 3,905,130 A | 9/1975 | Cordon et al. | 35/17 |
| 4,272,910 A | 6/1981 | Danz | 46/45 |
| 4,332,039 A | 6/1982 | LaFuente | 3/13 |
| 4,637,159 A | 1/1987 | Kulis | 43/42.32 |
| 5,004,443 A | 4/1991 | Su | 446/392 |
| 5,037,344 A | 8/1991 | Secrist | 446/392 |
| 5,061,279 A | 10/1991 | Friel | 623/4 |
| 5,108,427 A | 4/1992 | Majercik et al. | 623/4 |
| 5,733,333 A | 3/1998 | Sankey | 623/4 |
| 6,139,577 A | * 10/2000 | Schiepmann et al. | 623/6.64 |

* cited by examiner

Primary Examiner—Bruce Snow
(74) Attorney, Agent, or Firm—Weingarten, Shurgin, Gagnebin & Lebovici LLP

(57) ABSTRACT

An ocular prosthetic device is provided which includes a simulated pupil that does not interfere with the intended appearance of the iris image, and further which adapts to a range of ambient lighting environments to simulate the appearance of a natural eye. An iris image is provided to reproduce the color and pattern of a natural eye. A visual display, or light source, is located behind the iris image. The visual display has a series of concentric rings to produce a size range similar to the size range between that of a dilated and contracted pupil. The iris image has a pattern of light transmissive openings to permit light from the rearwardly disposed visual display to pass through the openings. The concentric rings, when activated, are visible through the openings in the iris image, and present the appearance of a pupil of a size dependent on the number of activated rings. When the rings are not activated, that is, when they are not darkened, the iris image, which overlies the deactivated rings, is visible such that the pupil appears more contracted. A light sensor located at the center of the visual display receives light through clear areas in the center of both the iris image and the visual display. By selectively activating and darkening increasingly sized rings in the series of concentric rings, the appearance of a pupil is provided. The sclera of a natural eye is also reproduced on the prosthetic eye.

19 Claims, 4 Drawing Sheets

DILATING OCULAR PROSTHESIS

CROSS REFERENCE TO RELATED APPLICATIONS

This application is a continuation-in-part of application Ser. No. 09/262,217, filed Mar. 4, 1999, now U.S. Pat. No. 6,139,577.

STATEMENT REGARDING FEDERALLY SPONSORED RESEARCH OR DEVELOPMENT

N/A

BACKGROUND OF THE INVENTION

Ocular prosthetic devices that simulate the appearance of a natural eye are known which attempt to faithfully reproduce the physical features of such a natural eye. Often such prosthetic eyes have a simulated iris of a color and pattern so as to match the complementary natural eye. Such prosthetic eyes typically incorporate an iris image, which nearly matches the complementary natural eye in color and pattern, and a simulated pupil. The iris image is produced on a white prosthetic shell adapted to be covered with a clear medium. The simulated pupil is of fixed size and does not react to light intensity, thereby detracting from the appearance of a natural eye. Attempts have been made to simulate a pupil which adjusts to light level so as to provide an appearance of pupil dilation and contraction in response to ambient light. One such approach is described in Danz, U.S. Pat. No. 4,272,910, which discloses a transparent annular display, located in front of an iris image, of a size approximating that of a fully dilated pupil. The transparent annular display is constructed such that it is darkened when activated to therefore provide the appearance of a fully dilated pupil. A light sensor, also having a darkened appearance, is located at the center of the transparent annular display to sense ambient light. The light sensor is of a size to provide the appearance of a fully contracted pupil. Based upon the signal from the light sensor, the transparent annular display can be darkened to give the appearance of a fully dilated pupil, by obscuring the centermost portion of the iris, or deactivated and made transparent such that the full iris image is seen and the darkened light sensor in the center appears as a fully contracted pupil.

Since the transparent annular display, however, is located in front of the iris image, the display tends to affect the appearance of the iris image even when it is deactivated. Further, as the display is activated to provide the appearance of a fully dilated pupil, such a display may not match the appearance of the pupil of the natural eye in moderate ambient lighting environments. Further, Danz does not suggest varying the display under a continuum of ambient lighting conditions to adapt to a variety of lighting environments.

Other prior art prosthetic eyes have not been satisfactory by reason of difficulty of manufacture, short useful life, poor natural appearance, or high cost. The following patents show prior art prosthetic eye constructions. Gordon et al., U.S. Pat. No. 3,905,130, discloses an opthalmological device including an eye mechanism using photographic-type diaphragms for simulating an iris. Gordon et al., however, utilizes a mechanical structure to alter pupil diameter, not an electronic display. Kulis, U.S. Pat. No. 4,637,159, teaches a simulated eye construction including a convex outer lens portion and a transparent second lens member having a reflecting surface behind for reflecting light. Kulis, however, does not teach pupil diameter adjustment. Secrist, U.S. Pat. No. 5,037,344, suggests an artificial doll eye which allows light to travel through a lens some distance into a solid, transparent light shaft in the center of the lens and pupil to give the impression of a real human eye. Secrist, however, does not suggest actual manipulation of pupil diameter. Su, U.S. Pat. No. 5,004,443, shows an electronically operated doll eyeball which uses LEDs to simulate movement of the pupil image, however does not disclose dynamically changing the apparent size of the pupil image.

It would be beneficial, therefore, to provide a prosthetic eye in which the iris color and pattern are consistent regardless of the simulated pupil size, and which provides a simulated pupil size adaptable to a variety of ambient lighting environments.

BRIEF SUMMARY OF THE INVENTION

An ocular prosthetic device is provided which includes a simulated pupil that does not interfere with the intended appearance of the iris image, and further which adapts in diameter to a range of ambient lighting environments to further simulate the appearance of a natural eye. An iris image, which reproduces the color and pattern of the complementary natural eye, is provided on a transparent plastic medium adapted to be integrated in a plastic prosthetic shell. A visual display, or light source, such as a liquid crystal display (LCD), is located behind the iris image. The visual display has a series of independently activated concentric rings to produce a size range similar to the size range between that of a fully dilated and fully contracted natural pupil. The iris image has a pattern of light transmissive openings to permit light from the rearwardly disposed visual display to pass through the openings. The concentric rings, when activated, are thereby visible through the openings in the iris image, and present the appearance of a pupil of a size dependent on the number of activated rings. When the rings are not activated, that is, when they are not darkened, the iris image, which overlies the deactivated rings, is visible such that the simulated pupil appears more contracted. A light sensor is located at the center of the visual display which receives light through clear areas in the center of both the iris image and the visual display. By selectively activating and darkening increasingly sized rings in the series of concentric rings, the appearance of a dilating and contracting pupil is provided through the openings in the iris image.

In another embodiment the ocular prosthetic device can include an image of the entire exposed eye comprising the pixilated iris, sclera and pupil printed or otherwise formed on a clear thermoplastic or other medium which is disposed on and adhered to the prosthetic shell. An entire normal eye can thereby be reproduced without the time and expense of hand painting and without the need for the skill of an ocularist to provide such hand painting.

BRIEF DESCRIPTION OF THE SEVERAL VIEWS OF THE DRAWING

FIG. 3b shows the actual size of the visual display of FIG. 3a;

DETAILED DESCRIPTION OF THE INVENTION

Figure 2:
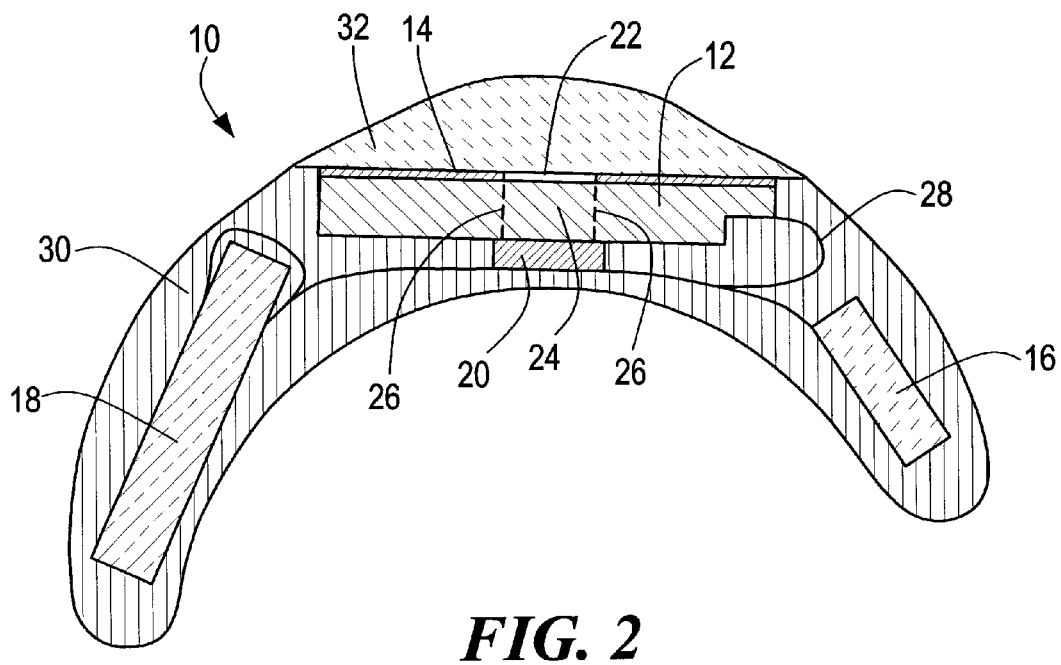
FIG. 2 shows a top sectional view of the prosthetic eye of FIG. 1 along line II.

Referring to FIG. 2, a prosthetic eye 10 according to the present invention is shown. In the embodiment shown, the transparent annular display is provided by a liquid crystal display 12, discussed further below, and is located behind the pixelated iris image 14 and connected to the control circuit 16 and battery 18. A light sensor 20 is also connected to the battery and control circuit, and is located behind the liquid crystal display 12. The light sensor 20 senses ambient light through clear area 22 in the center of the iris image 14 and clear area 24 in the center of the liquid crystal display 12, as indicated by dotted lines 26. The iris image 14, liquid crystal display 12, control circuit 16, and battery 18 are connected as indicated above by flexible circuitry 28, all of which are integrated in a white acrylic shell 30 and secured with a potting compound, which must be clear at least in the iris region. A clear acrylic front 32 secures the iris while allowing light to pass for activation of light sensor 20 and to allow for external observation of the pixelated iris image 14.

The iris image is preferable created from a digital photograph of the desired natural iris which is usually the iris of the user's good eye. The digital image is comprised of matrix of elements called pixels, and a number of pixels are removed from the digital image to provide clear, non-image areas. The digital photo is then color adjusted such that when it is viewed with the liquid crystal display visible through the pixels, the appearance has a color and pattern approximating that of the desired natural eye. The digital image is printed, or otherwise formed, on a transparent film such as an acetate film, in a size approximating that of a natural iris. The clear areas provided by the removed pixels in the original image are located in an annular area of the iris image surrounding the central pupil area and which will be disposed in front of the visual display. This iris image with pixels removed for light transmission or light porosity is referred to as a pixelated iris image.

Figure 1:
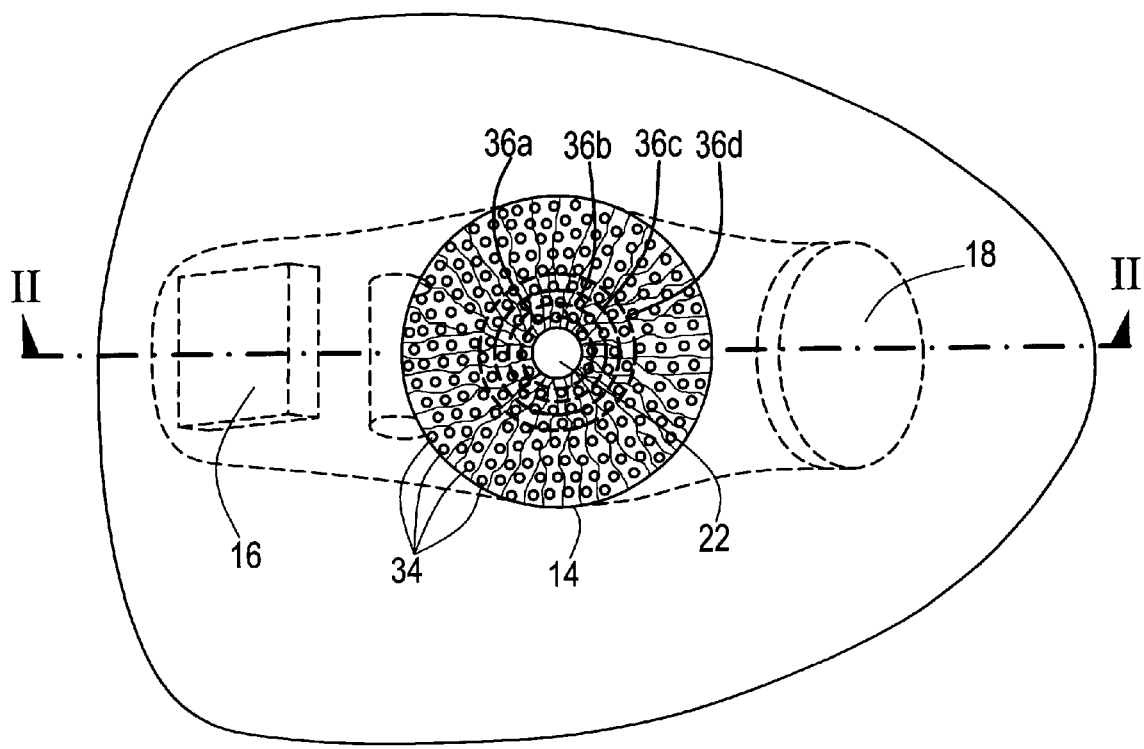
FIG. 1 shows a front view of the prosthetic device according to the present invention.

Referring to FIG. 1, pixelated iris image 14 is shown in more detail. The concentric rings 36a–36d are shown in dotted outline at the inner portion of the iris image 14. A clear area 22 in the center of the image accommodates a light sensor 20 (FIG. 2).

When an observer views the pixelated iris image 14, the liquid crystal display will also be visible through the pixelations 34 in the iris image. Since the digital photo is matched to approximate the color and pattern of the desired natural eye, the portions of the iris image with the inactivated display behind will appear as the natural iris color and pattern. As concentric rings 36a–36d are selectively activated and darkened, the portions of the iris with the activated liquid crystal display behind will appear as a pupil of various degrees of dilation. As indicated above, light sensor 20 has a darkened appearance and a size approximating that of a fully contracted pupil, and is at least in large in diameter as the clear areas 22, 24. When none of the concentric rings 36a–36d are activated, the light sensor 20 will still be visible through clear areas 22, 24 in the iris image and display, giving the appearance of a fully contracted pupil. When at least one of the concentric rings 36a–36d is activated and darkened, the appearance of the light sensor and the concentric rings will merge to have the appearance of a single darkened circle simulating a dilated pupil.

Figure 3A:
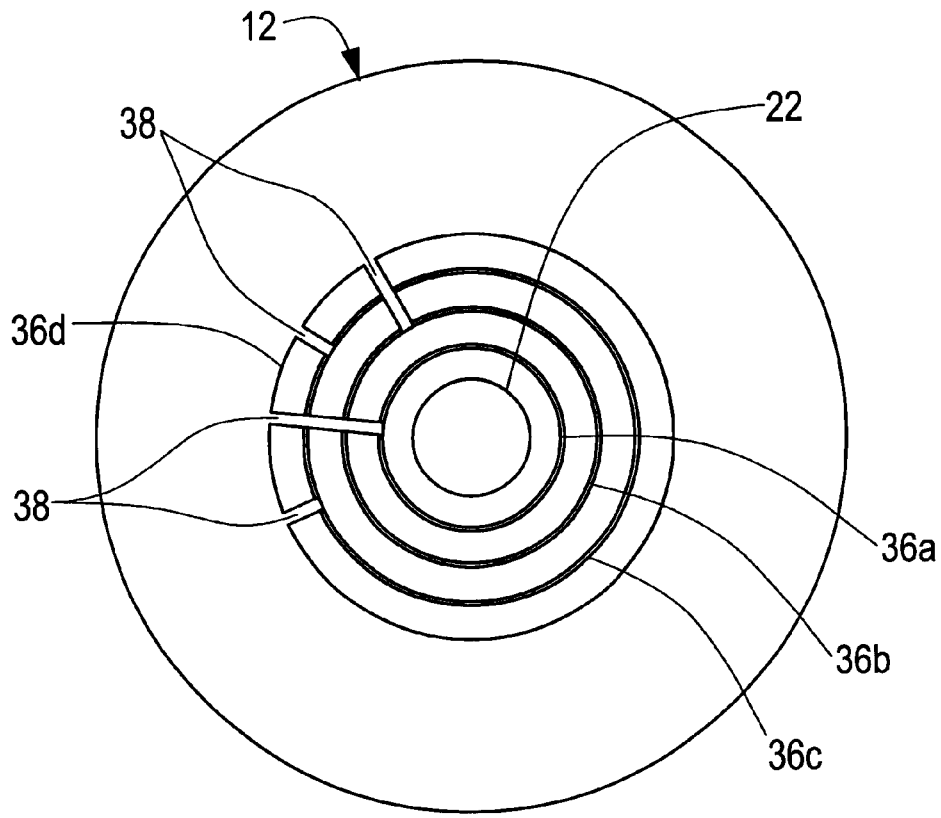
FIG. 3a shows one embodiment of the visual display according to the present invention.
Figure 3B:
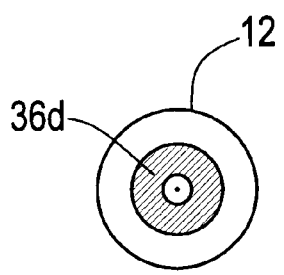

The liquid crystal display 12 is shown in enlarged size in FIG. 3a. As the concentric rings 36a–36d simulate the range of dilation and contraction of a pupil, the size of these rings ranges between that of a fully contracted and fully dilated pupil. In the present embodiment, the clear area 22 has an outside diameter of about 0.08 inches; the innermost ring 36a has an outside diameter of about 0.115 inches; the second ring 36b has an outside diameter of about 0.156 inches; the third ring 36c has an outside diameter of about 0.197 inches; and the outermost ring 36d has an outside diameter of about 0.238 inches, corresponding to the typical size of a fully dilated pupil. The outside diameter of the liquid crystal display 12 is preferably as close as possible to the outside diameter of the pixelated iris image, typically about 0.500 inches, so that the appearance of the iris image is consistent. Other sizes of simulated pupils and irises, however, could be used to simulate a particular natural eye size. In the present embodiment four rings are used to simulate the appearance of a pupil, however alternative embodiments may employ a greater number of rings to increase the granularity of adaptability to different ambient lighting levels. Gaps 38, discussed further below, are used to accommodate electronic traces for activating the respective rings of the liquid crystal display 12. FIG. 3b shows a typical actual size for a liquid crystal display 12 and outer diameter of concentric ring 36d according to the present invention.

Figure 4:
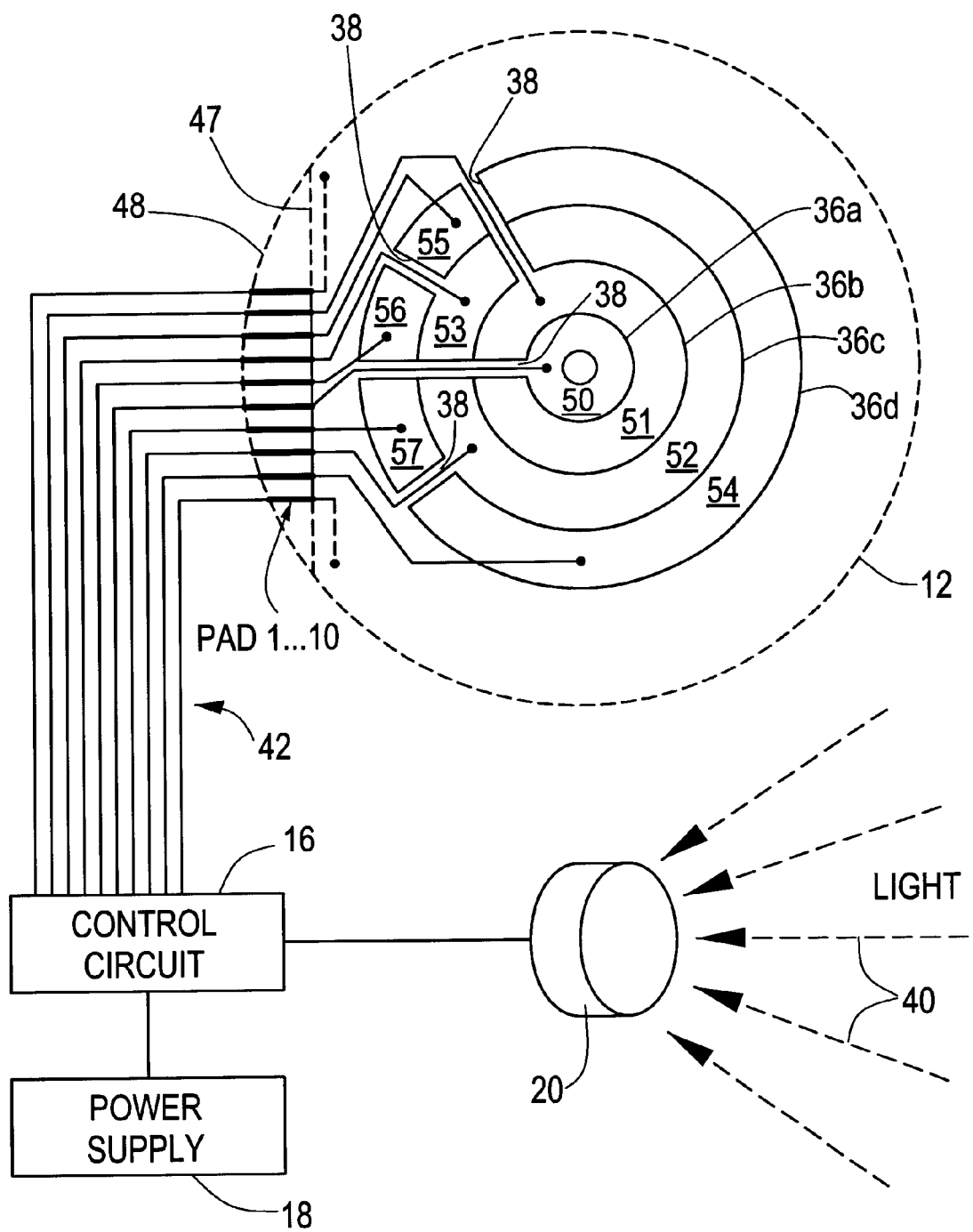
FIG. 4 shows a schematic of one embodiment of the pin and trace arrangement for activating the concentric rings of the visual display.

Referring to the schematic diagram of FIG. 4, the interconnection of the liquid crystal display 12 and the control circuit 16 are shown in more detail. Control circuit 16 receives input from light sensor 20 indicative of the intensity of ambient light 40. The light sensor can comprise elements such as a photodiode, a photodarlington, a photoconductor, or a photovoltaic, and is preferably of a size and shade similar to that of a fully contracted pupil. Concentric rings 36a–36d are selectively activated based on the level of ambient light. As a lesser ambient light would produce a dilated pupil in a natural eye, control circuit 16 activates all concentric rings 36a–36d when the level of ambient light drops below a predetermined threshold. As ambient light 40 increases, control circuit 16 selectively deactivates each outermost activated ring at a predetermined ambient light threshold, until all concentric rings 36a–36d are deactivated, thus giving the appearance of a fully contracted pupil.

Control circuit 16 activates concentric rings 36a–36d through control lines 42, each connected to a respective pad labeled pad1–pad10 on the liquid crystal display. As liquid crystal display 12 is a planar device, all connections must be on the same surface. Accordingly, concentric rings 36a–36d are subdivided into display portions to allow for traces to be connected to individual display portions 50–57 through gaps 38. Specifically, portion 50 of innermost ring 36a is activated through the trace from pad6; portion 51 of second ring 36b is activated through a trace from pad2; portions 52, 53 of third ring 36c are activated through traces from pad4 and pad8; and portions 54–57 of outermost ring 36d are activated by traces from pad3, pad5, pad7, and pad9. Pad1 and pad10 provide a ground through ground plate 48 which underlies and is similar in circumference to liquid crystal display 12 except for a flat portion, shown by dotted line 47, which allows electrical connection to pad1–pad10. As indicated above, power is provided by power supply 18, such as a NiCd, Ni metal hydride, or lithium battery. The battery supply is selected for maximum longevity, typically 2–5 years, and preferably is embedded in the prosthetic shell 30 with a colored marking to facilitate access after integration with the prosthetic shell.

Control circuit 16, therefore, activates each of the concentric rings 36a–36d by activating the control lines 42 connected to the display portions 50–57 of the particular rings. Concentric rings 36a–36d are separated by a minimal segment gap of about 0.003 inches in the embodiment shown. Similarly, gaps 38 are about 0.005 inches. In this manner, the concentric rings will appear as a continuous image of a pupil when viewed through the pixelated iris image 14.

Figure 5:
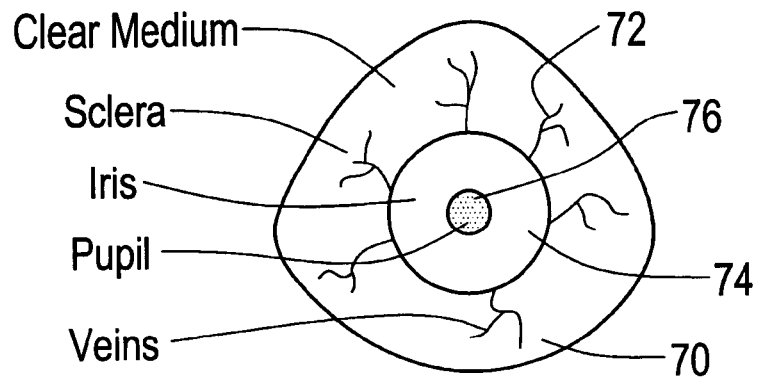
FIG. 5 is a plan view of a digitized image of an entire eye on a clear medium.
Figure 6:
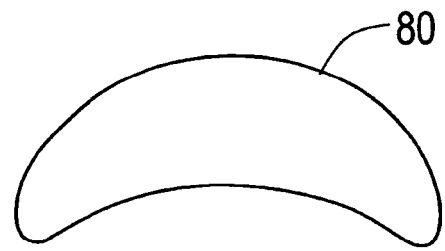
FIG. 6 is an elevation view of a prosthetic shell on which the digitized image is mounted.
Figure 7:
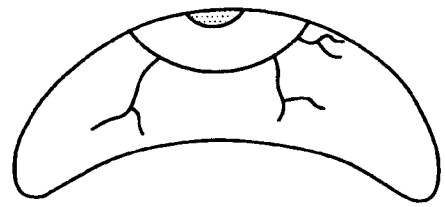
FIG. 7 is an elevation view of the digitized image of FIG. 5 mounted to the prosthetic shell of FIG. 6.

A further embodiment is shown in FIGS. 5–7 in which a reproduction of an entire normal eye is provided on the prosthetic eye. As shown in FIG. 5 a digitized image of an entire eye is printed or otherwise provided on a clear medium such as a thermoplastic film. The image includes the sclera 70, having veins 72 visible thereon, an iris area 74, and central pupil 76. The prosthetic shell 80 is shown in FIG. 6, and the film with the image thereon adhered to the prosthetic shell 80, as shown in FIG. 7. The film can be attached by heating and vacuum forming the film over the shell to adhere it to the surface of the shell. The pixelated iris image is provided as described above. The digitized image can be provided in similar manner to the iris image. A digital photograph of the desired natural eye is made usually from the user's good eye. The digital image is color adjusted such that when viewed the appearance has a color and pattern approximating that of the desired natural eye.

The present invention is not intended to be limited in scope by the specific embodiments described herein. As various extensions and modifications may be apparent to those skilled in the art, the present invention is not intended to be limited except as described in the following claims.

What is claimed is:

1. A prosthetic eye comprising:
    a prosthesis having a surface containing an image of a natural eye;
    an iris image having a plurality of holes therein corresponding to a predetermined pixelation pattern;
    an annular visual display having a plurality of concentric rings and operable for selective activation and deactivation of each of said concentric rings;
    a light sensor adapted to provide an ambient light signal; and
    a control circuit operable to selectively activate each of said concentric rings in response to said ambient light signal; wherein
        said annular visual display is visible through said pixelation pattern such that said iris image has an appearance of a first color and pattern when said rings are activated and a second color and pattern when said rings are deactivated.

2. The prosthetic eye of claim 1 wherein said first color and pattern are substantially similar to that of a pupil of a natural eye.

3. The prosthetic eye of claim 1 wherein said second color and pattern are substantially similar to that of an iris of a natural eye.

4. The prosthetic eye of claim 1 wherein said concentric rings are activated in a sequential order from said concentric rings having a smaller diameter to said concentric rings having a larger diameter.

5. The prosthetic eye of claim 4 wherein said concentric rings are deactivated in a sequential order from said concentric rings having a larger diameter to said concentric rings having a smaller diameter.

6. The prosthetic eye of claim 5 wherein said sequential order is a function of said ambient light signal.

7. The prosthetic eye of claim 6 wherein said sequential order is such that more concentric rings are activated when said ambient light signal is indicative of a lesser ambient light and fewer concentric rings are activated when said ambient light signal is indicative of a greater ambient light.

8. The prosthetic eye of claim 7 wherein said concentric rings are activated or deactivated when said ambient light signal is indicative of at least one predetermined threshold.

9. The prosthetic eye of claim 8 wherein said control circuit is operable to compare said ambient light signal to said at least one predetermined threshold wherein said selective activation is in response to the results of said comparing.

10. The prosthetic eye of claim 1 wherein said concentric rings are separated by a segment gap such that said concentric rings appear as a continuous image when said rings are viewed through said pixelation pattern in said iris image.

11. The prosthetic eye of claim 10 wherein at least one of said concentric rings further comprise a plurality of display portions, wherein each of said display portions are separated by a trace gap adapted to allow electrical connection from said control circuit to another of said concentric rings.

12. The prosthetic eye of claim 11 wherein each of said display portions is independently connected to and controlled by said control circuit.

13. The prosthetic eye of claim 11 wherein said trace gaps are such that said plurality of display portions appear as a continuous concentric ring when said display portions are viewed through said pixelation pattern in said iris image.

14. The prosthetic eye of claim 10 wherein said segment gap is about 0.003 inches.

15. The prosthetic eye of claim 11 wherein said trace gap is about 0.005 inches.

16. The prosthetic eye of claim 1 wherein said innermost concentric ring has an inside diameter of about 0.08 inches and said outermost concentric ring has an outside diameter of about 0.238 inches.

17. A method of forming a prosthetic eye comprising the steps of:
    providing a digitized visual image of a natural eye including the sclera and iris;
    pixelating the digital iris image to create a pixelated digital iris image having a predetermined pattern of transparent holes;
    providing a visual display having a darkened activated state and a lighter inactivated state;
    adjusting the color and pattern of the pixelated digital iris image such that the appearance of the iris image when viewed with the lighter, inactivated visual display behind and visible through the pixelated digital iris image approximates the appearance of said iris of a natural eye;
    printing onto a clear medium the reproduction of a natural eye including the pixelated digital iris image to form a simulated natural image;

disposing said visual display behind said simulated natural image such that said visual display is visible through said holes in the digital iris image;

connecting to said visual display a control circuit operable to selectively activate and thereby darken said visual display such that the appearance of said iris image when viewed with the darkened, activated display behind it approximates the appearance of the pupil of said natural eye.

18. The method of claim 17 wherein said visual display further comprises a plurality of concentric rings and wherein said control circuit is further operable to independently activate and deactivate each of said concentric rings.

19. The method of claim 18 wherein said selective activation and deactivation is in response to an ambient light signal indicative of surrounding ambient light.

* * * * *